United States Patent
Chiu et al.

(10) Patent No.: US 11,087,462 B2
(45) Date of Patent: Aug. 10, 2021

(54) SYSTEM AND METHOD FOR DETERMINING A COLONOSCOPY IMAGE

(71) Applicant: NATIONAL TAIWAN UNIVERSITY, Taipei (TW)

(72) Inventors: Han-Mo Chiu, Taipei (TW); Yi-Hsuan Chou, New Taipei (TW); Shuo-Hong Hung, Kaohsiung (TW); Li-Yang Chang, New Taipei (TW); Chung-Ping Chen, Taipei (TW)

(73) Assignee: National Taiwan University, Taipei (TW)

( * ) Notice: Subject to any disclaimer, the term of this patent is extended or adjusted under 35 U.S.C. 154(b) by 67 days.

(21) Appl. No.: 16/428,055

(22) Filed: May 31, 2019

(65) Prior Publication Data
US 2019/0370963 A1    Dec. 5, 2019

Related U.S. Application Data

(60) Provisional application No. 62/679,055, filed on Jun. 1, 2018.

(51) Int. Cl.
*G06T 7/00* (2017.01)
*G06T 5/00* (2006.01)
(Continued)

(52) U.S. Cl.
CPC .............. *G06T 7/0012* (2013.01); *A61B 1/31* (2013.01); *A61B 5/4255* (2013.01);
(Continued)

(58) Field of Classification Search
None
See application file for complete search history.

(56) References Cited

U.S. PATENT DOCUMENTS 7,440,601 B1 * 10/2008 Summers ........... G06K 9/00201
382/128
7,894,648 B2 * 2/2011 De Groen ............ G06T 7/0012
382/128
(Continued)

FOREIGN PATENT DOCUMENTS

CN        110020610 A  *  7/2019

OTHER PUBLICATIONS

A Novel Approach to Extract Colon Lumen from CT Images for Virtual Colonoscopy. Chen et al. (Year: 2000).*

(Continued)

*Primary Examiner* — Delomia L Gilliard
(74) *Attorney, Agent, or Firm* — Rosenberg, Klein & Lee (57) ABSTRACT

A system for determining a colonoscopy image is disclosed. The system includes a bowel preparation evaluation unit, an image processing unit electrically or communicatively connected to the bowel evaluation unit, and a convolutional neural network unit electrically or communicatively connected to the image processing unit. The bowel preparation evaluation unit determines whether a bowel in the colonoscopy image is clean. The image processing unit receives the colonoscopy image determined to have a clean bowel and outputted by the bowel preparation evaluation unit, and performs an image process on the colonoscopy image with clean bowel to adjust a contrast thereof. The convolutional neural network unit comprises a convolutional neural network and in a working mode, receives and determines whether the processed colonoscopy image is a cecal image, a non-cecal image, or an indeterminable colonoscopy image.

20 Claims, 6 Drawing Sheets

(51) Int. Cl.
*G06T 5/40* (2006.01)
*A61B 5/00* (2006.01)
*A61B 1/31* (2006.01)

(52) U.S. Cl.
CPC ............ *A61B 5/7267* (2013.01); *G06T 5/007* (2013.01); *G06T 5/40* (2013.01); *G06T 2207/20081* (2013.01); *G06T 2207/20084* (2013.01); *G06T 2207/30028* (2013.01); *G06T 2207/30096* (2013.01)

(56) References Cited

U.S. PATENT DOCUMENTS

| | | | | |
|---|---|---|---|---|
| 2005/0078858 | A1* | 4/2005 | Yao | G06T 7/149 382/128 |
| 2006/0047227 | A1* | 3/2006 | Jerebko | G06K 9/342 600/593 |
| 2007/0297662 | A1* | 12/2007 | Marzendorfer | G06T 11/008 703/11 |
| 2008/0055308 | A1* | 3/2008 | Dekel | G06T 15/08 345/421 |
| 2008/0117209 | A1* | 5/2008 | Razeto | G06T 7/136 345/424 |
| 2010/0021026 | A1* | 1/2010 | Collins | G06K 9/00 382/128 |
| 2011/0206250 | A1* | 8/2011 | McGinnis | G06T 7/0012 382/128 |
| 2013/0274602 | A1* | 10/2013 | Hernandez | A61B 8/4444 600/438 |
| 2016/0032363 | A1* | 2/2016 | Stintzi | C12Q 1/6883 514/503 |
| 2018/0110398 | A1* | 4/2018 | Schwartz | G06K 9/00496 |
| 2018/0253839 | A1* | 9/2018 | Zur | G06T 7/0012 |
| 2019/0080454 | A1* | 3/2019 | Hameed | A61B 1/0014 |
| 2019/0297276 | A1* | 9/2019 | Sachdev | G06T 7/0012 |

OTHER PUBLICATIONS

Improving Visual Quality in Wireless Capsule Endoscopy Images with Contrast-Limited Adaptive Histogram Equalization. Moradi et al. (Year: 2015).*

* cited by examiner

SYSTEM AND METHOD FOR DETERMINING A COLONOSCOPY IMAGE

REFERENCE TO RELATED APPLICATIONS

This non-provisional application claims priority claim under 35 U.S.C. § 119(a) on U.S. Provisional Patent Application No. 62/679,055 filed Jun. 1, 2018 the entire contents of which are incorporated herein by reference.

FIELD OF THE INVENTION

The invention relates to a system and a method for determining a colonoscopy image, more particularly, to a system and a method for determining a colonoscopy image through the use of deep learning technology.

BACKGROUND

In recent years, the number of colorectal cancer patients increases gradually and its incident rate and death rate are in the top five of the cancer ranking. Therefore, early finding and early treatment of colorectal cancer may prolong patient's life and even save patients from dying from colorectal cancer. The factors for colorectal cancer development are complex and currently it is believed to be associated with age, heredity, diet, gender and living habits, especially those whose family has a colorectal cancer history are more prone to develop colorectal cancer.

Currently the colorectal cancer can be detected through four methods: barium enema, fecal occult blood test, sigmoidoscopy, and colonoscopy. The barium enema uses barium as a contrast solution and when the barium concentration is not to a right range, it is possible to misinterpret the X-ray images. The fecal occult blood test is low cost, does not require bowel preparation, and is non-invasive, however, false positive results are often obtained and false negative may also result from vitamin C concentration in the subject. Sigmoidoscopy can only check the rectum and left side of the colon for polyps but not the right side of the colon and the cecum. The colonoscopy can check the entire large intestine from the rectum to the cecum for polyps but requires a doctor to operate a colonoscope to take the images inside the large intestine.

The quality of colonoscopy can be evaluated by indicators like adenoma detection rate, cecal intubation rate, bowel preparation quality and withdrawal times. Therefore, during colonoscopy, doctors would operate the colonoscope to take images and complete the colonoscopy by meeting the aforementioned indicator standards. However, if the doctor is inexperienced, the time took for the colonoscopy may be long and thereby causing the patient to be nervous and to have discomfort. Moreover, even if the aforementioned indicator standards are met, the colonoscope may not be operated deep enough into the cecum and thus the polyps in some parts of the colon may be missed or undetected.

SUMMARY

It is an object of the invention to provide a system for determining a colonoscopy image. The system includes a bowel preparation evaluation unit, an image processing unit electrically or communicatively connected to the evaluation unit, and a convolutional neural network unit electrically or communicatively connected to the image processing unit. The bowel preparation evaluation unit determines whether a bowel in a colonoscopy image is clean. The image processing unit receives the colonoscopy image determined to contain a clean bowel and outputted by the evaluation unit and performs an image process on the colonoscopy image with clean bowel to adjust a contrast thereof. The convolutional neural network unit includes a convolutional neural network, and in a working mode, receives the processed colonoscopy image and determines whether the processed colonoscopy image is a cecal image, a non-cecal image, or an indeterminable image.

Optionally, the system further includes a colonoscopy image capturing unit for capturing the colonoscopy image.

Optionally, the colonoscopy image capturing unit is a colonoscope electrically or communicatively connected to an end device, and the bowel preparation evaluation unit, the image processing unit, and the convolutional neural network unit are implemented through the hardware of a server or the combination of the software and hardware of the server, wherein the end device and the server are electrically or communicatively connected.

Optionally, the contrast of the colonoscopy image is adjusted by a histogram equalization process and/or a channel shift (i.e. pixel normalization).

Optionally, the image process further includes a down-sampling process or an over-sampling process to adjust a size of the colonoscopy image to a fixed size.

Optionally, the convolutional neural network unit receives, in a training mode, a plurality of training colonoscopy images for training the convolutional neural network, wherein the training colonoscopy image is a processed colonoscopy image with clean bowel.

Optionally, the convolutional neural network unit utilizes, in a training mode, at least one of a data augmentation process (such as, at least one of a rotation, a width shift, a height shift, a horizontal flip, a vertical flip, a zoom in, a zoom out and a channel shift), an early stopping process, a dropout process, and a filter parameter regularization process to prevent overfitting.

Optionally, the convolutional neural network unit divides, in the training mode, the plurality of training colonoscopy images into a first portion and a second portion, wherein the first portion of the training colonoscopy images serves as a training set, the second portion of the training colonoscopy images serves as a validation set, and a portion of the training colonoscopy images are randomly selected to serve as a testing set, wherein a ratio between the plurality of cecal images and the plurality of non-cecal images of the training colonoscopy images in the training set is m:1, wherein m is 0.5 through 1.5.

Another object of the invention is to provide a method for determining a colonoscopy image. The image determination method includes: in a training mode, receive a plurality of processed training colonoscopy images with clean bowel and train the convolutional neural network, wherein the plurality of training colonoscopy images are processed to enhance a contrast thereof; and in a working mode, receive a processed colonoscopy image with clean bowel and through the trained convolutional neural network, determine whether the received colonoscopy image is a cecal image, a non-cecal image, or an indeterminable colonoscopy image.

Optionally, the image determination method further includes: in the training mode, evaluate whether a bowel in each of the plurality of training colonoscopy images is clean, eliminate the training colonoscopy images with unclean bowel, and perform an image process on the training colonoscopy images with clean bowel, wherein the image process includes a pixel normalization, histogram equalization process and a downs-sampling process; and in the working mode, evaluate whether a bowel in each of the plurality of colonoscopy images is clean, and when the colonoscopy image is determined to contain a clean bowel, perform an image process on the colonoscopy image with clean bowel, wherein the image process includes a histogram equalization process and a down-sampling process.

BRIEF DESCRIPTION OF THE DRAWINGS

The structure as well as preferred modes of use, further objects, and advantages of this invention will be best understood by referring to the following detailed description of some illustrative embodiments in conjunction with the accompanying drawings, in which.

DETAILED DESCRIPTION OF THE PREFERRED EMBODIMENTS

According to embodiments of the invention, a system and method for determining a colonoscopy image are provided with the use of deep learning technology, wherein a convolutional neural network is implemented to act as a classifier to identify cecal images. First, a plurality of first colonoscopy images are collected and evaluated to eliminate any first colonoscopy image with unclean bowel. Then an image process is performed on the remaining first colonoscopy images for adjusting a contrast thereof, wherein the image process includes a histogram equalization process.

Then, the processed first colonoscopy images are used for training the convolutional neural network so as to identify the weight, bias, and multiple feature patterns corresponding to cecal images of each neuron in the convolutional neural network; the feature patterns are learnable filter patterns. The training of the convolutional neural network is complete once these parameters have been determined. Next, the trained convolutional neural network classifies a plurality of newly input second colonoscopy images with clean bowel, determining whether each of the second colonoscopy images is a cecal image, a non-cecal image, or an indeterminable colonoscopy image. Therefore, through the image determination system and method provided by the invention, doctors can know about the quality of the colonoscopy.

In on embodiment of the invention, during the training of the convolutional neural network, 90% of the remaining first colonoscopy images are randomly selected as a training set for training purpose, and the rest of the 10% are used as a validation set for validation purpose, but the selection method and ratio of the training set and validation set of the invention are not limited thereby. Moreover, the issue of overfitting during the training of the convolutional neural network is prevented by applying at least one of data augmentation, early stopping, dropout, and filter parameter regularization.

Figure 1A:
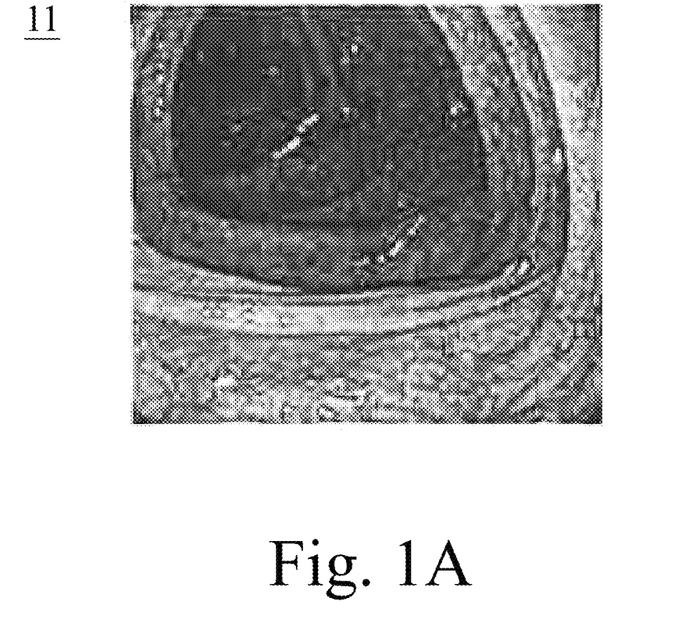
FIG. 1A is a schematic diagram illustrating a colonoscopy image being a non-cecal image according to an embodiment of the invention.
Figure 1B:
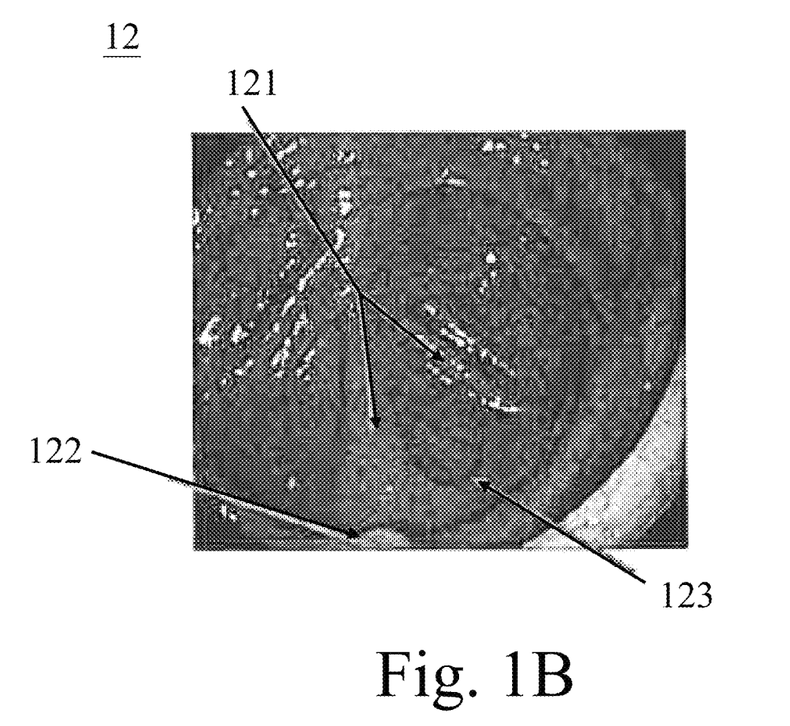
FIG. 1B is a schematic diagram illustrating a colonoscopy image being a cecal image according to an embodiment of the invention.

FIGS. 1A and 1B are schematic colonoscopy images illustrating a non-cecal image and a cecal image, respectively. A colonoscope is inserted into the large intestine through the rectum and hence before advancing to the cecum, the colonoscopy images taken inside the intestine are non-cecal images 11 as shown in FIG. 1A. Once the colonoscope reaches the cecum, the colonoscopy images taken are cecal images 12 as shown in FIG. 1B, wherein a few main characteristics can be found in the cecal image 12, for example, a fold 121, an ileocecal valve (ICV) 122, and an appendiceal orifice 123.

In short, the cecal image 12 has features which the non-cecal image 11 lacks and thus whether the colonoscopy images is a cecal image 12 or not can be determined by observing the colonoscopy images and looking for the aforementioned characteristics therein. However, besides putting in time and efforts, observation by human eyes also may result in false reading due to inexperience of the observer (doctor). Hence, to avoid the aforementioned issue, the invention utilizes a convolutional neural network as a classifier to interpret whether a colonoscopy image is a cecal image, so as to accurately determine a colonoscopy image to be a cecal image, a non-cecal image, or an indeterminable colonoscopy image.

Figure 1C:
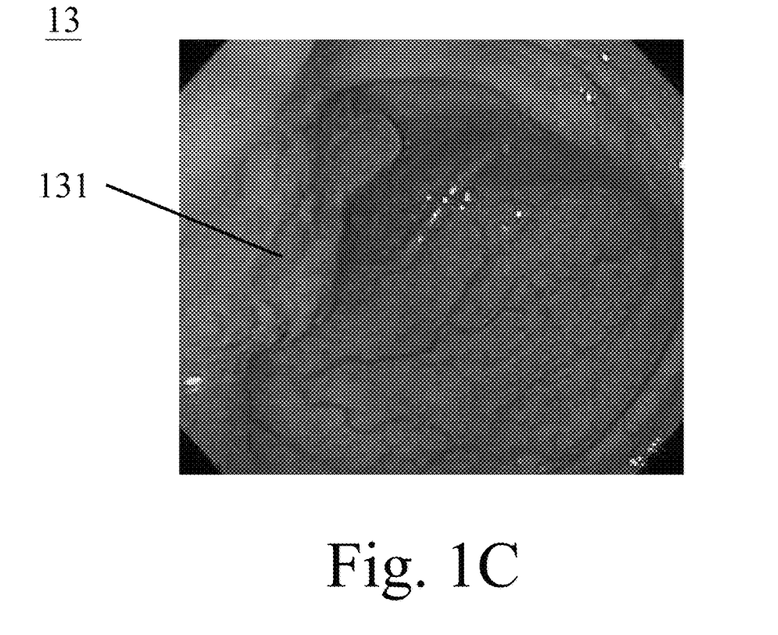
FIG. 1C and FIG. 1D are schematic diagrams illustrating colonoscopy images with unclean bowel.
Figure 1D:
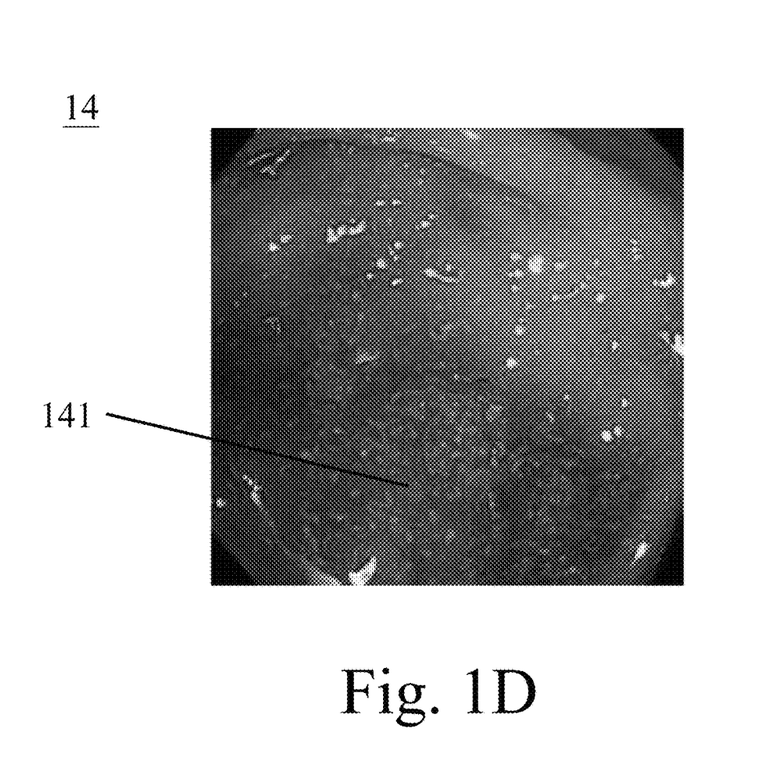

FIG. 1C and FIG. 1D are schematic diagrams illustrating colonoscopy images with unclean bowels. It is noted, each the colonoscopy images 13 and 14 has an unclean bowel since of excreta 131 and 141 exist in the bowels of the colonoscopy images 13 and 14. The excreta 131 and 141 will affect the determining decision, and before the colonoscopy images is input to convolutional neural network unit for determining, the colonoscopy images 13 and 14 with the unclean bowels should be picked out.

Figure 2:
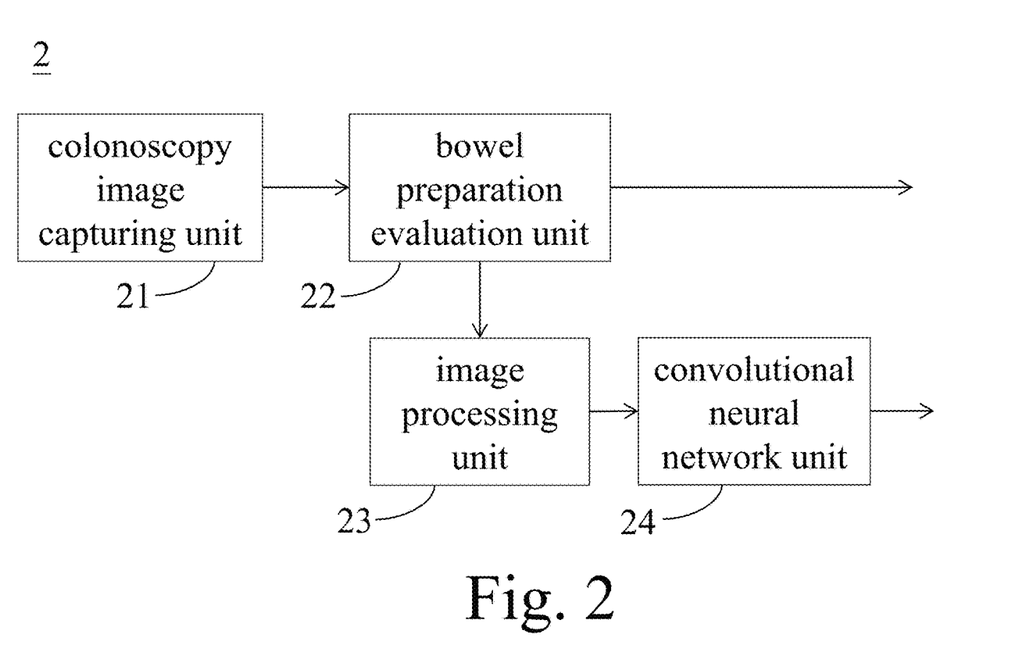
FIG. 2 is a functional block diagram of a system for determining a colonoscopy image according to an embodiment of the invention.

FIG. 2 is a functional block diagram of a system for determining a colonoscopy image according to a preferred embodiment of the invention. The image determination system 2 includes a colonoscopy image capturing device 21, a bowel preparation evaluation unit 22, an image processing unit 23, and a convolutional neural network unit 24. The colon image capturing device 21 is electrically or communicatively connected to the bowel preparation evaluation unit 22, the bowel preparation evaluation unit 22 is electrically or communicatively connected to the image processing unit 23, and the image processing unit 23 is electrically or communicatively connected to the convolutional neural network unit 24, wherein by electrically or communicatively connected means connection through conductive wire or wireless communication.

The colon image capturing unit 21 is a colonscope, which is inserted into the large intestine and the colon through the rectum and takes photographs to obtain a plurality of colonoscopy images. The plurality of colonoscopy images are divided into a plurality of first colonoscopy images and a plurality of second colonoscopy images, wherein the first colonoscopy images are used for training a convolutional neural network of the convolutional neural network unit 24 and the second colonoscopy images are determined by the convolutional neural network unit 24 whether each be a cecal image, a non-cecal image, or an indeterminable colonoscopy image. In other words, the first colonoscopy images are for use in a training mode and the second colonoscopy images are for use in a working mode.

The bowel preparation evaluation unit 22 evaluates and determines whether a bowel in the colonoscopy images is clean. If the bowel preparation was not done properly and feces exists in the colon, it would be difficult to determine whether the colonoscopy image is a cecal image, a non-cecal image, or an indeterminable colonoscopy image, and also cannot accurately check for polyps in the colon. Therefore, the bowel preparation evaluation unit 22 screens out the colonoscopy images that contain unclean bowel so they are not sent to the image processing unit 23 and correspondingly outputs an unclean bowel signal to indicate the current colonoscopy image is defected with unclean bowel.

The image processing unit 23 performs an image process on the colonoscopy image with clean bowel to enhance a contrast of the colonoscopy image. In general, a colonoscopy image that is too bright or too dark is harder to identify whether it has charactertistics of a cecal image due to insufficient contrast, and so an improvement on the contrast is needed for the colonoscopy image with low contrast. In one embodiment of the invention, the image process includes a histogram equalization process to enhance the contrast, but the invention is not limited thereby. For example, a pixel normalization (or channel shift) which normalizes pixel value from [0, 255] to [−1,+1] can be also used to adjust the contrast.

In other words, the contrast of the first colonoscopy images with clean bowel and the second colonoscopy images with clean bowel is adjusted by the image processing unit 23 before the first and second colonoscopy images with clean bowel are output to the convolutional neural network unit 24. On the other hand, for the convolutional neural network of the convolutional neural network unit 24 to have a fixed size, the image processing unit 23 further performs sampling on the colonoscopy images, like a down-sampling process or an over-sampling process, such that the size of each colonoscopy image is the fixed size, like a fixed size of 3×128×128 pixels, wherein 3×128×128 represents three images of primary colors R, G, B with length and width of 128×128 pixels.

The convolutional neural network unit 24 includes a convolutional neural network that serves as a classifier for determining whether a colonoscopy image is a cecal image, a non-cecal image, or an indeterminable colonoscopy image. The convolutional neural network includes a plurality of neurons. In a training mode, the weight and bias of each neuron are adjustable, and the size and parameters of multiple feature patterns corresponding to cecal images are also adjustable, wherein the feature patterns are learnable filter patterns.

Furthermore, in the training mode, by inputting some or all of the plurality of first colonoscopy images and the result of each being a cecal or non-cecal image as a training set into the convolutional neural network, the convolutional neural network learns and determines the weight, bias, and multiple feature patterns corresponding to cecal images of each neuron. Therefore, the trained convolutional neural network can act as a classifier for determining whether a colonoscopy image is a cecal image, a non-cecal image, or an indeterminable colonoscopy image. Then, in a working mode, the convolutional neural network unit 24 is able to determine each of the plurality of processed second colonoscopy images to be either a cecal image, a non-cecal image, or an indeterminable colonoscopy image.

In one embodiment of the invention, during the training of the convolutional neural network, 90% of the plurality of first colonoscopy images with clean bowel are randomly selected as a training set for training purpose and the remaining 10% of the plurality of first colonoscopy images with clean bowel after the random selection is used as a validation set for validation purpose. It is to be noted that the selection method and ratio of the training set and the validation set of the invention is not limited thereby. In this embodiment, about 50% of the plurality of first colonoscopy images are selected as a testing set, and preferably the ratio of cecal images and non-cecal images is approximately m:1 in the testing set for precisely evaluating the accuracy, wherein m is 0.5 through 1.5, and more preferably, m can be 1. An advantage of the validation set is to further ensure the network structure or parameters controlling model complexity, whereas the testing set can only be used to check the efficiency of the best model that has been finally selected. It is to be noted that the selections of the training set, the validation set, and the testing set of the invention are not limited thereby.

In addition, when training the convolutional neural network, at least one of a data augmentation process, an early stopping process, a dropout process, and a filter parameter regularization process is utilized to prevent the issue of overfitting. Data augmentation is to modify the plurality of first colonoscopy images to create more first colonoscopy images for training the convolutional neural network, and comprises at least one of a rotation, a width shift, a height shift, a horizontal shift, a horizontal flip, a vertical flip, a zoom in, a zoom out and a channel shift. For example, the first colonoscopy images are rotated at 90 degrees, 180 degrees, and 270 degrees to create more first colonoscopy images that can be used to train the convolutional neural network, thereby the number of first colonoscopy images used for training is quadrupled.

Moreover, early stopping is a process where the validation set is used after a few epochs (an epoch refers to a complete training process in which one forward pass and one backward pass of all the training examples has been performed), like every five epochs, to obtain test result of the model. With the increasing of epochs, once the validation set detects a rise in test error, the training is terminated and the current trained model is set to be the working model.

Dropout is a process of reducing neural network layers or neurons/nodes/units to prevent adaptation of the neural network, for example, randomly dropping out the units at a probability of 0.2 during training, but the invention is not limited thereby.

Filter parameter regularization is a process where a punish is added into the cost function so as to limit some parameters. If a weight is too large, the cost would be excessive, and so the weight is punished after backpropagation to keep the weight be a smaller value. L1 regularization and L2 regularization are common filter parameter regularizations, and in this embodiment, L1 regularization can be used, but the invention is not limited thereby.

Figure 3:
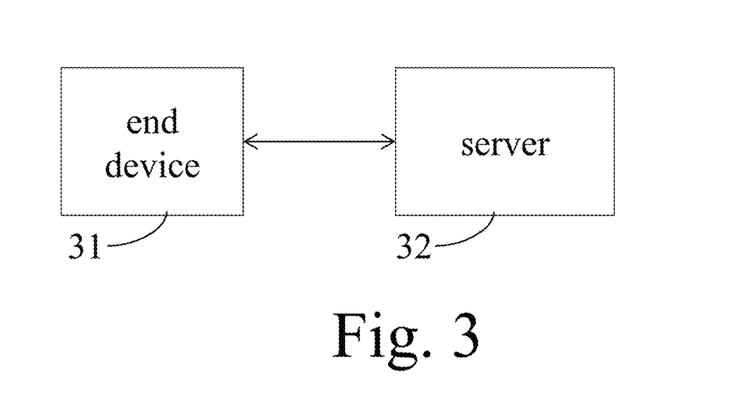
FIG. 3 is a functional block diagram of a system for determining a colonoscopy image according to another embodiment of the invention.

FIG. 3 is a functional block diagram of a system for determining a colonoscopy image according to another embodiment of the invention and depicts an end device 31 and a server 32 that are electrically or communicatively connected to each other. In this embodiment, the colonoscopy image capturing unit 21 of FIG. 2 is implemented by a colonoscope electrically or communicatively connected to the end device 31, the bowel preparation evaluation unit 22, the image processing unit 23, and the convolutional neural network unit 24 are implemented through the hardware of the server 32 or the combination the software and hardware of the server 32.

In other words, all the related computations are processed by the server 32 which has better computation capability, and the doctors only need to operate the colonocope electrically or communicatively connected to the end device 31 to obtain the plurality of colonoscopy images and upload the obtained colonoscopy images via the end device 31. The server 32 then is able to use the first colonoscopy images of the plurality of colonoscopy images for training purpose and/or determines/classifies the second colonoscopy images of the plurality of colonoscopy images. Also, in some circumstances, the bowel preparation evaluation unit 22 may be implemented through the hardware of the end device 31 or the combination the software and hardware of the end device 31, and so is the image processing unit 23.

It is noted that, the server 32 may operate in the training mode, and the end device 31 may operate in the working mode. That is, the server 32 and the end device 31 have the components of the image determination system 2, the server 32 is designed for the training mode while the end device 31 is designed for the working mode, and the server 32 sets the convolution neutral network of the end device 31 after the training has been finished.

Figure 4:
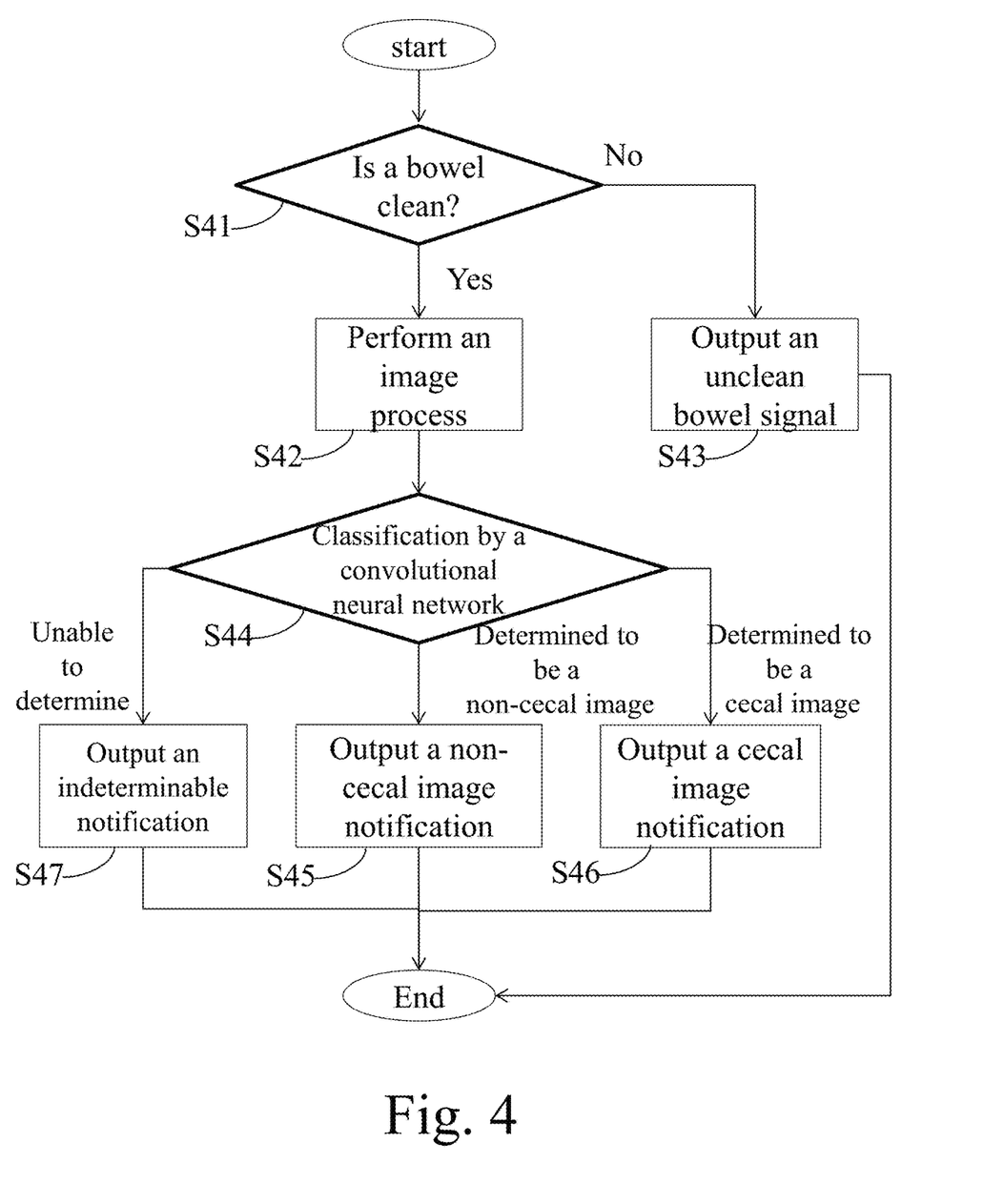
FIG. 4 is a flowchart of a method for determining a colonoscopy image according to an embodiment of the invention.

FIG. 4 is a flowchart of a method for determining a colonoscopy image according to one embodiment of the invention. The method may be implemented by a single electronic device with computation capability or by a cooperation of several electronic devices with computation capabilities. FIG. 4 depicts the method in working mode, and the method further includes steps of using a plurality of first colonoscopy images to train a convolutional neural network in training mode, wherein the method of training the convolutional neural network is as aforementioned, and therefore will not be described herein.

First, in step S41, evaluate whether a bowel in each of a plurality of second colonoscopy images that has been input is clean. If the bowel is clean, step S42 is executed, and if the bowel is not clean, step S43 is executed. In step S42, the second colonoscopy image with clean bowel undergoes an image process to affix a size and to adjust a contrast of the second colonoscopy image. In step S43, an unclean bowel notification/signal is output.

Subsequently, in step S44, the processed second colonoscopy image is classified by a trained convolutional neural network. If the trained convolutional neural network determines the processed second colonoscopy image to be a non-cecal image, step S45 is executed to output a non-cecal image notification. If the trained convolutional neural network determines the processed second colonoscopy image to be a cecal image, step S46 is executed to output a cecal image notification. If the trained convolutional neural network cannot determine the classification of the processed second colonoscopy image, then step S47 is executed to output an indeterminable notification.

Figure 5A:
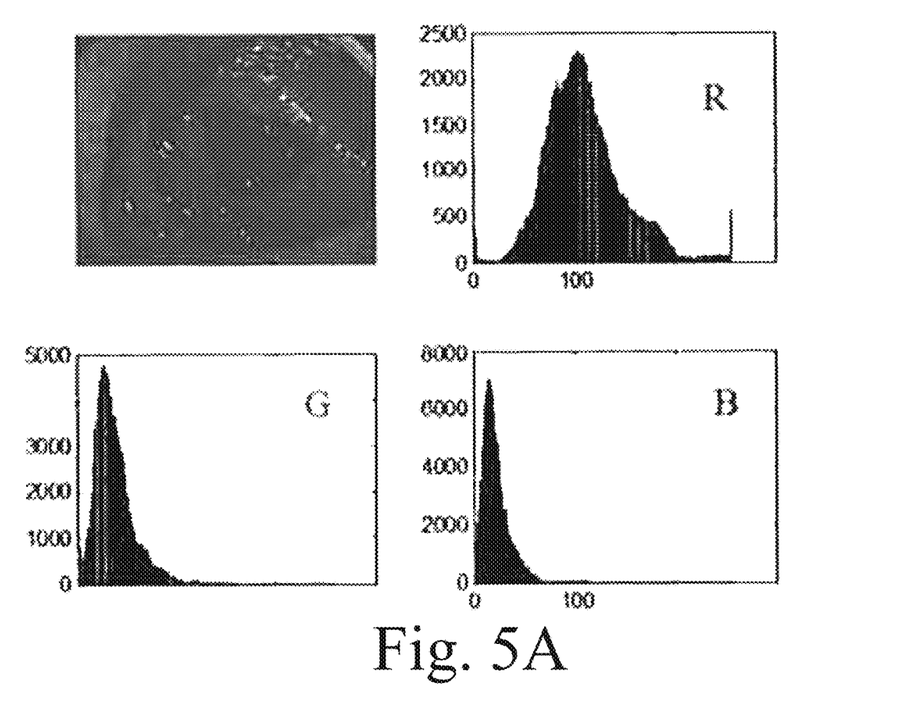
FIG. 5A depicts schematic diagrams illustrating a contrast of a second colonoscopy image according to an embodiment of the invention.

FIG. 5A depicts schematic diagrams illustrating a contrast of a second colonoscopy image according to one embodiment of the invention. Referring to FIG. 5A, the second colonoscopy image is at upper left hand side and its grayscale histograms of three primary colors R, G, B are respectively at upper right hand side, lower left hand side, and lower right hand side. It can be seen that the original second colonoscopy image has a lot of pixels, which would lead to an enormous amount of computations when input to the convolutional neural network for classification and training. Moreover, the grayscale of the pixels are not scattered in distribution but concentrated in a specific region, and thus the contrast of the second colonoscopy image as a whole is lower.

Figure 5B:
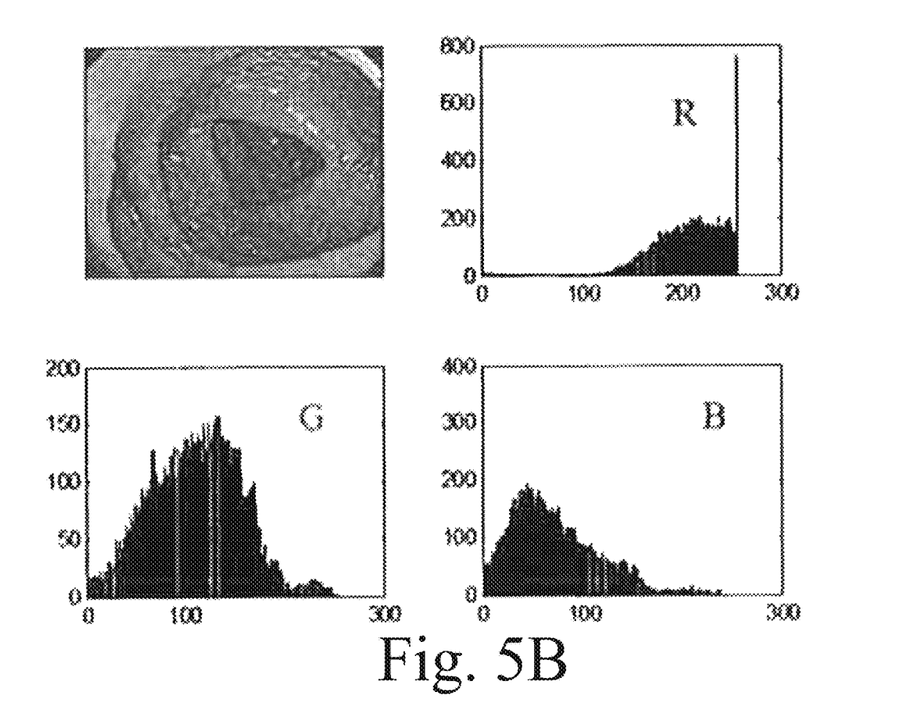
FIG. 5B depicts schematic diagrams illustrating a contrast of a processed second colonoscopy image according to another embodiment of the invention.

FIG. 5B depicts schematic diagrams illustrating a contrast of a second colonoscopy image after undergone image processing according to one embodiment of the invention. The image process in this embodiment includes a down-sampling process and a histogram equalization process, and the contrast of the second colonoscopy image in FIG. 5A after being processed is as shown in FIG. 5B. Referring to FIG. 5B, the processed second colonoscopy image is at upper left hand side and its grayscale histograms of three primary colors R, G, B are respectively at upper right hand side, lower left hand side, and lower right hand side. It can be seen from FIG. 5B that the number of pixels in the processed second colonoscopy image is decreased and so if it were to be input to the convolutional neural network for classification or training, the computation would not be excessive. Furthermore, the grayscale of the pixels are scattered in distribution shown in the grayscale histograms of three primary colors R, G, B in FIG. 5B, not concentrated in a specific region, and therefore the contrast of the entire processed second colonoscopy image is enhanced.

Figure 6:
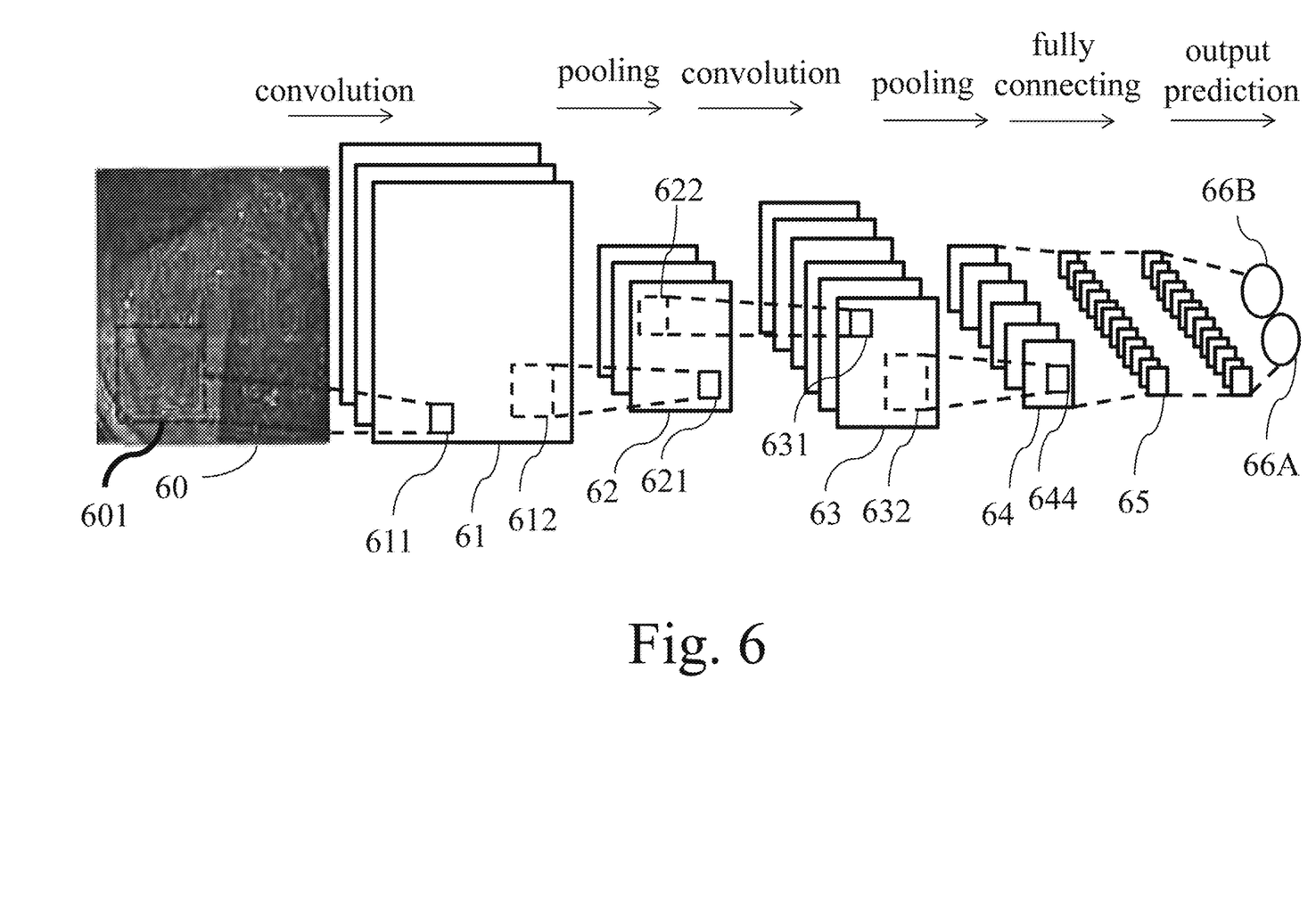
FIG. 6 is a schematic diagram illustrating an architecture of a convolutional neural network implemented in a convolutional neural network unit according to an embodiment of the invention.

FIG. 6 is a schematic architecture diagram of a convolutional neural network utilized in a convolutional neural network unit according to one embodiment of the invention. The convolutional neural network unit 24 in FIG. 2 may utilize the architecture shown in FIG. 6. A convolutional neural network generally consists convolutional layer, pooling layer, and connecting layer. Referring to FIG. 6, a colonoscopy image 60 is input to a first convolutional layer, wherein each block 601 of the colonoscopy image 60 goes through a convolution operation with multiple feature patterns before being put in a rectified linear operation to generate a plurality of feature blocks 611 in a plurality of feature maps 61. Next, the plurality of feature maps 61 are input to a first pooling layer, wherein every block 612 of each feature map 61 goes through a pooling operation to generate a corresponding pooling value 621 in a pooling map 62. The pooling operation can be a maximum pooling operation or an average pooling operation and the invention is not limited thereby.

Subsequently, the plurality of pooling maps 62 are input to a second convolutional layer, wherein a block 622 of the pooling map 62 goes through a convolution operation with multiple feature patterns before being put in a rectified linear operation to generate a plurality of feature blocks 631 of a plurality of feature maps 63. Then, the plurality of feature maps 63 are input to a second pooling layer, wherein every block 632 of each feature map 63 goes through a pooling operation to generate a corresponding pooling value 644 in a pooling map 64. The pooling operation is a maximum pooling operation or an average pooling operation, and the invention is not limited thereby.

Next, the plurality of pooling values 644 of the pooling maps 64 are input to each input neuron 65 of a fully connecting layer, wherein the fully connecting layer would conduct computation and generate an output prediction result to each output neuron 66A, 66B. The output prediction results at the output neurons 66A and 66B are probabilities respectively indicating a probability of cecal images and a probability of non-cecal images. The fully connecting layer is in fact a neural network having an input layer with a plurality of input neurons 65, an output layer with output neurons 66A and 66B, and at least one hidden layer with a plurality of middle neurons, wherein the hidden layer is disposed between the input layer and the output layer.

It is to be noted that other types of convolutional neural network can also be used in the invention. For example, the convolutional neural network architecture of Visual Geometry Group (VGG) can also be applied in the invention. Additionally, a partially connecting layer can also be used as the connecting layer instead of the fully connecting layer shown in FIG. 6. The convolutional neural network type of the invention is not limited thereby.

In conclusion, the system and method for determining a colonoscopy image according to the embodiments of the invention train the convolutional neural network by inputting a plurality of colonoscopy images and then the trained convolutional neural network serves as a classifier to determine whether a colonoscopy image is a cecal image automatically, and thus in comparison to the conventional technology, the invention does not require manpower for image classification/determination and is advantageous in automation, high accuracy, and time efficiency of determining colonoscopy images.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

What is claimed is:

1. A system for determining a colonoscopy image, the system comprising:
    a bowel preparation evaluation unit for determining whether a bowel in a colonoscopy image is clean;
    an image processing unit electrically or communicatively connected to the bowel preparation evaluation unit, for receiving the colonoscopy image determined to contain a clean bowel and outputted by the bowel preparation evaluation unit and performing an image process on the colonoscopy image with clean bowel to adjust a contrast thereof; and
    a convolutional neural network unit electrically or communicatively connected to the image processing unit and comprising a convolutional neural network, wherein in a working mode, the convolutional neural network unit receives and determines whether the processed colonoscopy image is a cecal image, a non-cecal image, or an indeterminable colonoscopy image.

2. The system of claim 1, further comprising:
    a colonoscopy image capturing unit for capturing the colonoscopy image.

3. The system of claim 2, wherein the colonoscopy image capturing unit is a colonoscope.

4. The system of claim 3, wherein the colonoscopy is electrically or communicatively connected to an end device, the bowel evaluation unit, the image processing unit, and the convolutional neural network unit are implemented through the hardware of a server or the combination of the software and hardware of the server, and the server and the end device are electrically or communicatively connected.

5. The system of claim 3, wherein the bowel evaluation unit, the image processing unit, and the convolutional neural network unit are implemented through the hardware of an end device or the combination of the software and hardware of the end device, the end device operates in the working mode, and a server operates in a training mode for setting the convolutional neural network of the end device.

6. The system of claim 3, wherein the colonoscopy is electrically or communicatively connected to an end device, the bowel evaluation unit is implemented through the software and hardware of the end device, the convolutional neural network unit is implemented through the hardware of a server or the combination of the software and hardware of the server, the image processing unit is implemented through the hardware of the end device or the combination of the software and hardware of the end device, or the hardware of the server or the combination of the software and hardware of the server, and the end device and the server are electrically or communicatively connected.

7. The system of claim 1, wherein the contrast of the colonoscopy image is adjusted by a histogram equalization process and/or a channel shift.

8. The system of claim 1, wherein the image process further comprises a down-sampling process or an over-sampling process to adjust a size of the colonoscopy image to a fixed size.

9. The system of claim 1, wherein in a training mode, the convolutional neural network unit receives a plurality of training colonoscopy images for training the convolutional neural network, and the training colonoscopy images are processed colonoscopy images with clean bowel.

10. The system of claim 9, wherein in the training mode, the convolutional neural network unit utilizes at least one of a data augmentation process, an early stopping process, a dropout process, and a filter parameter regularization process to prevent overfitting.

11. The system of claim 9, wherein in the training mode, the convolutional neural network unit divides the training colonoscopy images into a first portion and a second portion, wherein the first portion of the training colonoscopy images serves as a training set, the second portion of the training colonoscopy images serves as a validation set.

12. The system of claim 9, wherein in the training mode, the convolutional neural network unit randomly selects a portion of the training colonoscopy images to be a testing set, and a ratio between cecal images and non-cecal images is m:1 in the testing set, wherein m is 0.5 through 1.5.

13. A method for determining a colonoscopy image, the method comprising:
    in a working mode:
    receiving a colonoscopy image determined to contain a clean bowel and undergone an image process; and
    through a convolutional neural network, determining whether the processed colonoscopy image with clean bowel is a cecal image, a non-cecal image, or an indeterminable colonoscopy image.

14. The method of claim 13, further comprising:
    in the working mode:
    evaluating whether a bowel in the colonoscopy image is clean; and
    when the bowel in the colonoscopy image is determined to be clean, performing the image process on the colonoscopy image with clean bowel.

15. The method of claim 13, wherein the image process comprises a histogram equalization process and/or a channel shift.

16. The method of claim 13, wherein the image process comprises a down-sampling process or an over-sampling process.

17. The method of claim 13, further comprising:
    in a training mode:
    receiving a plurality of training colonoscopy images for training a convolutional neural network, the training colonoscopy images being determined to contain clean bowel and undergone an image process, wherein the image process enhances a contrast of the training colonoscopy images.

18. The method of claim 17, further comprising:

in the training mode:

evaluating whether a bowel in the training colonoscopy image is clean;

eliminating the training colonoscopy image with unclean bowel; and performing the image process on the training colonoscopy image with clean bowel.

19. The method of claim 17, wherein in the training mode, at least one of a data augmentation process, an early stopping process, a dropout process, and a filter parameter regularization process is utilized to prevent overfitting.

20. The method of claim 17, wherein in the training mode, the training colonoscopy images are divided into a first portion and a second portion, wherein the first portion of the training colonoscopy images serves as a training set, the second portion of the training colonoscopy images serves as a validation set; a portion of the training colonoscopy images are randomly selected to be a testing set, and a ratio between cecal images and non-cecal images is m:1 in the testing set, wherein m is 0.5 through 1.5.

* * * * *